United States Patent [19]

Boehning et al.

[11] Patent Number: 4,829,043

[45] Date of Patent: May 9, 1989

[54] SILVER CATALYST AND A PROCESS FOR ITS PREPARATION

[75] Inventors: Karl-Heinz Boehning, Darmstadt; Wolf D. Mross, Frankenthal; Matthias Schwarzmann, Limburgerhof; Hans-Juergen Becker, Neustadt; Juergen Plueckhan; Klaus-Christian Renner, both of Frankenthal, all of Fed. Rep. of Germany

[73] Assignee: BASF Aktiengesellschaft, Ludwigshafen, Fed. Rep. of Germany

[21] Appl. No.: 134,150

[22] Filed: Dec. 17, 1987

[30] Foreign Application Priority Data

Dec. 18, 1986 [DE] Fed. Rep. of Germany ....... 3643248

[51] Int. Cl.$^4$ .................... B01J 21/04; B01J 23/04; B01J 23/50
[52] U.S. Cl. ..................... 502/348; 549/534
[58] Field of Search .................. 502/341, 347, 348

[56] References Cited

U.S. PATENT DOCUMENTS

| | | | |
|---|---|---|---|
| 2,294,383 | 9/1942 | Carter | 260/348 |
| 3,172,893 | 3/1965 | Ameen | 260/348.5 |
| 3,423,328 | 1/1969 | Keith et al. | 252/430 |
| 3,725,307 | 4/1973 | Brown et al. | 502/347 |
| 3,962,136 | 6/1976 | Nielsen et al. | 252/454 |
| 4,010,115 | 3/1977 | Nielsen et al. | 252/454 |
| 4,012,425 | 3/1977 | Nielsen et al. | 260/348.5 R |
| 4,033,903 | 7/1977 | Maxwell | 252/476 |
| 4,102,820 | 7/1978 | Cavitt | 252/463 |
| 4,206,128 | 6/1980 | Cavitt | 260/348.34 |
| 4,321,206 | 3/1982 | Cavitt | 260/348.34 |
| 4,324,699 | 4/1982 | Mross et al. | 502/347 |
| 4,356,312 | 10/1982 | Nielsen et al. | 549/534 |
| 4,368,144 | 1/1983 | Mitsuhata et al. | 252/463 |
| 4,663,303 | 5/1987 | Becker et al. | 502/348 X |
| 4,690,913 | 9/1987 | Nojori et al. | 502/340 |
| 4,740,493 | 4/1988 | Boehning et al. | 502/348 |

FOREIGN PATENT DOCUMENTS

| | | |
|---|---|---|
| 0172565 | 2/1986 | European Pat. Off. |
| 0211397 | 2/1987 | European Pat. Off. |
| 2300512 | 7/1973 | Fed. Rep. of Germany. |
| 2712785 | 9/1977 | Fed. Rep. of Germany. |
| 3010533 | 10/1980 | Fed. Rep. of Germany. |
| 2043481 | 10/1980 | United Kingdom. |

*Primary Examiner*—W. J. Shine
*Attorney, Agent, or Firm*—Keil & Weinkauf

[57] ABSTRACT

A silver catalyst containing lithium and cesium as promoters for the direct oxidation of ethylene with oxygen to give ethylene oxide is applied to a porous carrier and essentially consists of α-alumina and contains certain amounts of soluble calcium, aluminum, potassium and sodium salts. The carrier has a BET surface area of from 0.4 to 0.8 m$^2$/g, a pore volume of not less than 0.45 ml/g, the pores being equally accessible to cold and warm water, a bulk density of less than 700 kg/m$^3$ and a shape which, in the reactor, provides a geometrical surface area of not less than 600 m$^2$/m$^3$, on which more than 13% by weight of silver are applied as active component and more than 115 kg of silver are available per m$^3$ of reactor, and from 100 to 300 ppm by weight of lithium and from 200 to 600 ppm by weight of cesium are present as promoters. A process for the preparation of the silver catalyst and its use for the oxidation of ethylene are described.

5 Claims, No Drawings

SILVER CATALYST AND A PROCESS FOR ITS PREPARATION

It is known that silver-containing catalysts can be used for the direct oxidation of ethylene with oxygen to give ethylene oxide. α-alumina is generally used as a carrier for the preparation of the silver catalyst. There are various known processes for applying the catalytically active component silver to the carrier (U.S. Pat. Nos. 2,294,383, 3,423,328 and 3,172,893).

There are discrepancies in the literature concerning the desirable properties for the carrier. As a rule, therefore, very wide ranges for the physical properties of the carrier are claimed in patents.

Thus, German Laid-Open Application DOS No. 3,010,533 specifies surface areas of less than 1 m$^2$/g, a pore volume from 0.2 to 0.6 cm$^3$/g and a pore diameter of from 500 to 50,000 nm. The chemical composition of the carrier is said not to be critical. 700 kg/m$^3$ is stated as a possible bulk density.

In German Laid-Open Application DOS No. 2,712,785 carriers having BET surface areas of from 0.03 to 2 m$^2$/g and a pore volume of from 0.25 to 0.65 cm$^3$/g are described as being particularly suitable. U.S. Pat. No. 3,962,136 comes to similar conclusions.

Suitable carriers are also disclosed in, for example, German Laid-Open Application DOS No. 2,655,738. However, no catalysts doped with alkali metals, as claimed in the present Application, are prepared or investigated in the Examples.

In these catalysts, however, the composition of the components and the doping are not optimal. The importance of the alkali metals as promoters is disclosed per se, for example in German Laid-Open Application DOS No. 2,300,512 or DOS No. 2,753,359. However, the carrier used there does not correspond to the most recent state of the art.

In contrast, the most recent technical experience shows that only small sections of the known ranges of carriers and promoters have truly advantageous properties in the catalysts produced. Surprisingly good results in terms of activity, selectivity and especially catalyst life are obtained in the direct oxidation of ethylene with oxygen to give ethylene oxide using a silver catalyst on a porous carrier of α-alumina which contains certain amounts of soluble calcium, potassium and sodium salts and has a BET surface area of from 0.4 to 0.8 m$^2$/g, a pore volume of not less than 0.45 ml/g, the pores being equally accessible to cold and warm water, a bulk density of less than 700 kg/m$^3$ and a shape which, in the reactor, provides a geometrical surface area of not less than 600 m$^2$/m$^3$, on which more than 13% by weight of silver are applied as active component and more than 110 kg of silver are available per m$^3$ of reactor, the catalyst additionally containing from 100 to 300 ppm by weight of lithium and from 200 to 600 ppm by weight of cesium.

The carrier which is important with regard to the activity of the catalysts is produced form alumina and should contain not less than 99% by weight of α-Al$_2$O$_3$. The contents of ionic calcium and/or aluminum compounds soluble in nitric acid may be from 200 to 2,000 ppm, and the contents of soluble potassium and/or sodium compounds should not exceed 50 ppm. The carrier of very pure α-Al$_2$O$_3$ should advantageously have a BET surface area of not less than 0.4 m$^2$/g and not more than 0.8 m$^2$/g. The pore volume of the carrier is advantageously determined by the generally known method of water absorption or mercury porosimetry. The pore volume determined by the action of water for only 5 minutes at room temperature should not differ significantly, for example by no more than 10%, from the volume determined by the stated methods.

The pore distribution may be bimodal or unimodal; in the bimodal case, the larger pores preferably account for not less than 50% of the total pore volume and have a mean diameter of about 10,000 to 40,000 nm and the smaller pores have a diameter of about 500 to 2,000 nm, and in the unimodal case the mean pore diameter is from 1,000 to 5,000 nm. By choosing suitable geometrical shapes for the carrier particles, the bulk density of the carrier can be adjusted so that its does not exceed 700 kg/m$^3$ and the outer geometrical surface area of the catalyst per reactor volume does not fall below 600 m$^2$/m$^3$.

The catalytically active metal components are applied by an impregnating process which may consist of one or more impregnation steps and comprises one or more heating steps. The catalytically active components are applied by impregnating the carrier in one or more stages with a silver salt solution, which contains complex-forming additives, and alkali metal salt solutions and heating the product, likewise in one or more stages. The catalyst carrier should be brought into contact with not less than 13% by weight of silver, and the resulting amount of silver should be not less than 110 kg per m$^3$ of reactor; the content of lithium should be from 100 to 300 ppm by weight of the content of cesium from 200 to 600 ppm by weight.

The novel silver catalysts are used for the preparation of ethylene oxide from ethylene and oxygen in the gas phase. The advantage is that, when used for the preparation of ethylene oxide, these catalysts have good initial selectivity and their selectivity decreases only by about half the amount observed in the case of the known catalysts; consequently, the lives are longer. At the same time, the catalysts exhibit greater flexibility with regard to space velocity. The activity too increases, so that lower reactor temperatures are possible.

EXAMPLES

The preparation of the novel catalysts and of the catalysts not according to the invention (comparative catalysts) on various carriers is carried out in the following manner:

Silver nitrate is dissolved in twice the molar amount of sec-butylamine. 1 ml of an aqueous lithium nitrate solution (for example 22.75 g of LiNO$_3$ per 100 ml of solution) is added per batch of this solution for 100 g of carrier. The volume of the solution is then increased 1.1-fold by adding fully demineralised water.

The carrier is impregnated with the solution in an amount corresponding to the expected liquid absorption of the carrier and is stored for one day at room temperature. The impregnated carrier is then transferred to a through-circulation drier and heated at 240° C. in a stream of nitrogen until the reaction has died down.

In a second impregnation step, the catalyst is treated with an amount of a methanolic solution sufficient for complete impregnation and containing 1% by volume of sec-butylamine and 1 ml of a cesium hydroxide solution (for example 5.46 CsOH per 100 ml of solution in methanol). This is followed by a drying step in a stream of nitrogen.

Alternatively, the carrier may be impregnated with the cesium solution (without the addition of methanol) at the same time as the silver salt solution.

However, it is also possible to apply the promoters lithium and cesium to the carrier before deposition of silver.

The stated contents of lithium and cesium (Tables 1 and 2) are optimized in separate experiments for the particular carrier used.

EXAMPLE 1

The abovementioned catalysts are comminuted, and in each case 10 g of the sieve fraction 0.6–0.75 nm are introduced into a stainless steel reactor having an internal diameter of 5 mm. The reactor has a jacket through which a thermostating liquid is passed. A gas composed of 30% of ethylene, 8% of oxygen and 2ppm of inhibitor, the remainder being nitrogen, is passed through the reactor. The pressure is 16 bar and the space velocity is 3,300 l (S.T.P.) of gas per l of catalyst per hour. The temperature is adjusted so that the oxygen conversion is 50%. After 2 days, samples are taken and the activity and selectivity determined.

The advantageous results of the reaction which can be achieved using the catalyst prepared on the carriers A and B are summarized in Table 3, the values shown being the mean values of various measurements. The less advantageous results obtained with all other carriers (C-K) are shown in the second part of the Table.

All three variants of the catalyst impregnation as described above may be used.

velocity of 4,000 m³ (S.T.P.) of gas per m³ of catalyst per hour. Samples are taken in each case after one month and after 12 months.

Table 4 shows the life characteristics and the flexibility in the space velocity of the catalysts used.

The novel carriers have the properties summarized in Table 1 below. Similar known carriers having properties which differ in various respects are shown in Table 2. These carriers do not have the desired advantageous properties as shown in the Examples below.

TABLE 1

Physical and chemical data of the novel carriers and catalysts

| Carrier designation | A | B |
|---|---|---|
| Content of $\alpha$-$Al_2O_3$ [% by weight] | 99.8 | 99.1 |
| Content of $SiO_2$ [% by weight] | 0.1 | 0.6 |
| Content of ions soluble in $HNO_3$ [ppm by weight] | | |
| Al | 250–2,000 | 150–2,000 |
| Ca | 150–2,000 | 50–2,000 |
| K | 20–1,000 | 20–1,000 |
| Na | 50–1,000 | 80–1,000 |
| BET surface area [m²/g] | 0.70 | 0.60 |
| Water absorption [ml/g] | | |
| cold | 0.45 | 0.42 |
| boiling | 0.50 | 0.45 |
| Bulk density [kg · m³] | 620 | 700 |
| Specific surface area [m²/m³] | 640 | 670 |
| Silver density [kg/m³] | 115 | 120 |
| Silver content [% by weight] | 13 | 15 |
| Lithium content [ppm by weight] | 100 | 250 |
| Cesium content [ppm by weight] | 450 | 400 |
| Catalyst designation | A | B |

TABLE 2

Properties of carriers and catalysts not according to the invention

| Carrier designation | C | D | E | F | G | H | I | A | B |
|---|---|---|---|---|---|---|---|---|---|
| Content of $\alpha$-$Al_2O_3$ [% by weight] | 99.8 | 99.5 | 99.8 | 99.8 | 99.8 | 98.5 | 99.6 | | |
| Content of $SiO_2$ [% by weight] | 0.1 | 0.4 | 0.1 | 0.05 | 0.04 | 1.4 | 0.1 | | |
| Content of ions soluble in $HNO_3$ [ppm by weight] | | | | | | | | | |
| Al | 250 | 600 | 300 | 100 | 150 | 60 | 130 | | |
| Ca | 350 | 500 | 400 | 100 | 100 | 10 | 300 | | |
| K | 20 | 40 | 30 | 5 | 5 | 2 | 10 | | |
| Na | 30 | 80 | 80 | 60 | 100 | 50 | 20 | | |
| BET surface area [m²/g] | 0.45 | 0.50 | 0.50 | 0.35 | 0.35 | 0.35 | 0.25 | | |
| Water absorption [ml/g] | | | | | | | | | |
| cold | 0.34 | 0.33 | 0.35 | 0.39 | 0.28 | 0.31 | 0.22 | | |
| boiling | 0.43 | 0.42 | 0.43 | 0.48 | 0.35 | 0.35 | 0.25 | | |
| Bulk density [kg/m³] | 730 | 730 | 600 | 650 | 810 | 810 | 1050 | | |
| Specific surface area [m²/m³] | 670 | 670 | 570 | 630 | 630 | 630 | 670 | | |
| Silver density [kg/m³] | 100 | 100 | 90 | 105 | 110 | 110 | 85 | | |
| Silver content [% by weight] | 12 | 12 | 12 | 14 | 10 | 10 | 8 | 13 | 15 |
| Lithium content [ppm by weight] | 150 | 100 | 200 | 130 | 100 | 150 | 140 | — | 250 |
| Cesium content [ppm by weight] | 300 | 250 | 350 | 200 | 300 | 150 | 150 | 450 | — |
| Catalyst designation | C | D | E | F | G | H | I | J | K |

EXAMPLE 2

Catalysts A, B, C, F and I, in the uncomminuted form, are each introduced in an amount of 13 dm³ into a steel pressure-resistant reactor which corresponds to the individual tube conventionally used in industrial plants. The reactor has a jacket through which a thermostating liquid is passed. A gas composed of 30% of ethylene, 8% of oxygen, 6.5% of $CO_2$, 4% of argon, 3 ppm of inhibitor and 50% of methane is passed through the reactor. The pressure is 16 bar. The temperature of the cooling medium of the reactor is adjusted in a preliminary test series a so that a space velocity of 2,000 m³ (S.T.P.) of gas per m³ of catalyst per hour coupled with an oxygen conversion of 35% is achieved. In a second test series, 50% of the oxygen is converted at a space

TABLE 3

Results of the experiments according to use Example 1

| Carrier | Selectivity [%] | Activity [%] |
|---|---|---|
| A | 82.3 | 217 |
| B | 82.2 | 218 |
| C | 81.9 | 222 |
| D | 81.9 | 225 |
| E | 81.5 | 227 |
| F | 81.0 | 221 |
| G | 80.9 | 224 |
| H | 80.1 | 230 |
| I | 80.0 | 226 |
| J | 81.0 | 225 |

TABLE 3-continued

| Results of the experiments according to use Example 1 | | |
| --- | --- | --- |
| Carrier | Selectivity [%] | Activity [%] |
| K | 76.0 | 210 |

TABLE 4

| Results of the experiments according to use Example 2 | | | |
| --- | --- | --- | --- |
| Carrier | Selectivity [%] at 35% $O_2$ conversion | Activity [%] at 35% $O_2$ conversion | Selectivity [%] at 50% $O_2$ conversion | Activity [%] at 50% $O_2$ conversion |
| After 1 month | | | |
| A | 82.5 | 196 | 81.5 | 220 |
| B | 82.5 | 197 | 81.3 | 220 |
| C | 82.1 | 200 | 80.4 | 226 |
| F | 81.5 | 200 | 80.0 | 228 |
| I | 81.0 | 204 | 79.5 | 234 |
| After 12 months | | | |
| A | 81.5 | 200 | 80.4 | 228 |
| B | 81.6 | 205 | 80.4 | 230 |
| C | 80.5 | 210 | 79.0 | 238 |
| F | 80.2 | 208 | 78.4 | 242 |
| I | 79.4 | 213 | 77.0 | 249 |

We claim:

1. A silver catalyst containing lithium and cesium as promoters for the direct oxidation of ethylene with oxygen to give ethylene oxide comprising a porous carrier consisting essentially of not less than 99% by weight of $\alpha$-$Al_2O_3$ produced from alumina and from 200 to 2,000 ppm of soluble calcium ions, from 200 to 2,000 ppm of soluble aluminum ions, more than 50 ppm of soluble potassium ions and more than 50 ppm of soluble sodium ions, said carrier having a BET surface area of from 0.4 to 0.8 $m^2/g$, a pore volume of not less than 0.45 ml/g, the pores being equally accessible to cold and warm water, a bulk density of less than 700 $kg/m^3$ and a shape which, in a reactor, provides a geometrical surface area of not less than 600 $m^2/m^3$, and having applied thereon more than 13% by weight of silver, as active component, more than 110 kg of silver being available per $m^3$ of reactor, and from 100 to 300 ppm by weight of lithium and from 200 to 600 ppm by weight of cesium.

2. The silver catalyst of claim 1, wherein said carrier contains very pure $\alpha$-$Al_2O_3$.

3. A process for the preparation of the silver catalyst defined in claim 1, wherein the catalytically active components are applied by impregnating the carrier in one or more stages with a silver salt solution which contains alkali metal salt solutions and heating the impregnated product, in one or more stages, the catalyst carrier being brought into contact with not less than 13% by weight of silver and the resulting mass of silver being not less than 110 kg per $m^3$ of reactor, and the content of lithium being from 100 to 300 ppm by weight and the content of cesium from 200 to 600 ppm by weight.

4. The silver catalyst of claim 1, wherein the pore distribution in bimodal, the larger pores have a mean diameter of from 10,000 to 40,000 nm and the smaller pores have a diameter of from 500 to 2,000 nm, said larger pores accounting for not less than 50% of the total pore volume.

5. The silver catalyst of claim 1, wherein the pore distribution is unimodal, the pores having a mean pore diameter of from 1,000 to 5,000 nm.

* * * * *